United States Patent [19]

Pelosi, Jr. et al.

[11] 4,012,415
[45] Mar. 15, 1977

[54] 2-[5-(3,4-DIMETHOXYPHENYL)-2-FURYL-]IMIDAZOLE HYDROCHLORIDE

[75] Inventors: Stanford S. Pelosi, Jr.; Chia-Nien Yu, both of Norwich, N.Y.

[73] Assignee: Morton-Norwich Products, Inc., Norwich, N.Y.

[22] Filed: Jan. 29, 1976

[21] Appl. No.: 653,446

[52] U.S. Cl. .............................. 260/309; 424/273; 260/346.1 R; 260/347.7
[51] Int. Cl.² ....................................... C07D 405/04
[58] Field of Search ................................... 260/309

[56] References Cited

UNITED STATES PATENTS 2,710,870  6/1955  Lawson ........................... 260/309
3,600,399  8/1971  Berkelhammer et al. ......... 260/309

FOREIGN PATENTS OR APPLICATIONS 1,215,858  12/1970  United Kingdom ............... 260/309

OTHER PUBLICATIONS

Schubert et al., Chem. Abst., 1963, vol. 58, cols. 2445–2446.

*Primary Examiner*—Natalie Trousof
*Attorney, Agent, or Firm*—Anthony J. Franze

[57] ABSTRACT

2-[5-(3,4-Dimethoxyphenyl)-2-furyl]imidazole hydrochloride is an effective antihypertensive agent.

1 Claim, No Drawings

2-[5-(3,4-DIMETHOXYPHENYL)-2-FURYL]IMIDAZOLE HYDROCHLORIDE

This invention relates to the compound 2-[5-(3,4-dimethoxyphenyl)-2-furyl]imidazole hydrochloride of the formula:

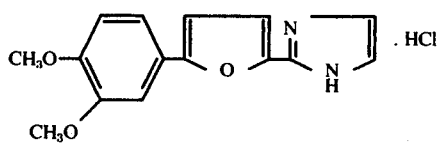

This compound possesses pharmacologic activity. In particular it exhibits antihypertensive activity when administered intraperitoneally to warm-blooded animals. Thus, when administered intraperitoneally in a pharmaceutically acceptable solvent, such as saline, at a dose of 50 mg/kg to unanesthetized spontaneously hypertensive rats, reduction in the arterial blood pressure is elecited.

This compound is preferably prepared in accordance with the following example:

To 248 g (1.3 m) of 3,4-dimethoxyaniline hydrochloride in 1 l of water was added 300 ml of concentrated HCl. After cooling to −5°–0°, a solution of 91 g (1.3 m) of sodium nitrite in 300 ml of water was added in about 1 hr while maintaining the temperature at −5°–2°. After further stirring at the same temperature range for 1½ hr, 210 g of solid sodium acetate was added to adjust the pH to ca. 3.5. Then a solution of 72 g of cupric chloride dihydrate in 400 ml of water and 252 g (2.6 m) of furfural in 500 ml of water was added. The mixture was allowed to stir for 8 days and then extracted with toluene. The toluene extract was washed with water and dried over $MgSO_4$. After filtering off $MgSO_4$, the toluene filtrate was concentrated in a water bath at reduced pressure. The excess furfural was also distilled off in a boiling water bath at reduced pressure. A dark viscous liquid residue weighing 292 g was obtained.

Part of the above dark viscous liquid (287 g) was stirred with 4 l of SDA-32 and filtered. The filtrate was concentrated to half of its original volume and then heated at reflux with 172 g (2.48 m) of hydroxylamine hydrochloride and 202 g (2.48 m) of anhydrous sodium acetate in 400 ml of water. After 4 hr of reflux, the mixture was allowed to cool slightly and then poured onto crushed ice. Gummy material separated at first and gradually solidified on standing. The solid was collected, washed well with water and air dried. The yield was 156 g. Recrystallization from a 50/50 mixture of isopropanol/$H_2O$ gave, in two crops, 70.5 g (22%) of 5-(3,4-dimethoxyphenyl)-2-furaldehyde oxime. An analytical sampel melted at 140° – 142°.

A mixture of 70.5 g (0.29 m) of the above oxime in 650 ml of acetic anhydride was heated at reflux for 3 hr. After slight cooling, the solution was poured onto crushed ice with stirring in a 4 l beaker. The solid was collected, washed well with water and air dried. The yield was 49.3 g (77.5%). Recrystallization of 45 g from 1.8 l of SDA-32 gave 37 g of dark brown crystalline 5-(3,4-dimethoxyphenyl)-2-furonitrile. An analytical sample melted at 151° – 153°.

Into a mixture of the recrystallized 5-(3,4-dimethoxyphenyl)-2-furonitrile (20 g) in 500 ml of absolute ethanol was bubbled HCl gas for 2 hr with some cooling. The mixture was filtered and the green solid was washed with some anhydrous ether and dried in a vacuum desiccator. Two more crops were obtained by addition of ether to the filtrate. Total yield was 24 g (86%) of ethyl 5-(3,4-dimethoxyphenyl)-2-furimidate hydrochloride.

A mixture of 52.0 g (0.167 mole) of ethyl 5-(3,4-dimethoxyphenyl)-2-furimidate hydrochloride, 19.3 g (0.184 mole) of aminoacetaldehyde dimethyl acetal and 800 ml of anhydrous methanol was heated to reflux with dissolution. The solution was refluxed for 5 hours and the solvent was then removed on the Calab evaporator yielding a residual oil which was stirred in 800 ml of 3N HCl for ca. 20 hours at a temperature of 70°. The resulting solid was washed in refluxing acetic acid, filtered hot and dried at 100° to yield 14.5 g (28%) of 2-[5-(3,4-dimethoxyphenyl)-2-furyl]imidazole hydrochloride. An analytical sample was prepared by washing a sample a second time in refluxing acetic acid and drying in the vacuum piston at the temperature of refluxing water, m.p. 288°–289°.

Anal. Calc'd for $C_{15}H_{14}N_2O_3 \cdot HCl$: C, 58.73; H, 4.93; N, 9.13. Found: C, 58.77; H, 4.98; N, 9.02.

What is claimed is:

1. The compound 2-[5-(3,4-dimethoxyphenyl)-2-furyl]imidazole hydrochloride.

* * * * *